United States Patent [19]

Bitton et al.

[11] Patent Number: 5,149,656
[45] Date of Patent: Sep. 22, 1992

[54] MICROBIOLOGICAL ASSAY PAD AND KIT FOR SELECTIVE DETECTION OF TOXICANTS

[75] Inventors: Gabriel Bitton; Ben Koopman, both of Gainesville, Fla.

[73] Assignee: University of Florida Research Foundation, Inc., Gainesville, Fla.

[21] Appl. No.: 518,686

[22] Filed: May 3, 1990

[51] Int. Cl.[5] ............................................. C12M 1/40
[52] U.S. Cl. ..................................... 435/288; 435/4; 435/18; 435/21; 435/29; 435/805; 435/968; 435/970; 435/810; 435/975
[58] Field of Search ................................ 435/291-805, 435/968, 970, 288, 810, 975, 7.9, 18, 4, 21, 29

[56] References Cited

U.S. PATENT DOCUMENTS 5,030,555  7/1991  Clemmons ........................ 435/311
5,037,735  8/1991  Khanna et al. .................... 435/7.6

OTHER PUBLICATIONS

Mueller-Hill, B., H. V. Rickenberg, K. Wallenfels (1964) "Specificity of the Induction of the Enzymes of the Lac Operon in *Escherichia coli*," J. Mol. Biol. 10:303-318.

Freifelder, D. (1989) "Regulation of the Activity of Genes in Prokaryotes," In *Molecular Biology*, Jones and Bartlett Publishers, Inc., Portola Valley, Calif., pp. 456-473.

Mazidji, C. N., B. N. Koopman, G. Bitton, G. Voiland (1990) "Use of Microtox ® and Ceriodaphinia Bioassays in Wastewater Fractionation," Toxicity Assessment: An International Journal vol. 5:265-277.

Kuehl, D. W., G. T. Ankley, L. P. Burkhard, D. Jensen (1990) "Bioassay Directed Characterization of the Acute Aquatic Toxicity of a Creosote Leachate," Hazardous Waste & Hazardous Materials 7(3):283-291.

Primary Examiner—Johnnie R. Brown
Assistant Examiner—Pamela S. Webber
Attorney, Agent, or Firm—Saliwanchik & Saliwanchik

[57] ABSTRACT

Described here are procedures and kits for the selective detection of toxicants in environmental samples. Specifically exemplified are procedures and kits which are used to detect heavy metals. The presence of heavy metals is detected by observing the inhibition by the toxicant of a microbially produced enzyme.

13 Claims, No Drawings

MICROBIOLOGICAL ASSAY PAD AND KIT FOR SELECTIVE DETECTION OF TOXICANTS

BACKGROUND OF THE INVENTION

It is well documented that a great variety of pollutants can be found throughout the environment. Pollutants may be, for example, polar and non-polar compounds, detergents, and heavy metals. The accurate identification of specific types of pollutants present in a water or soil sample facilitates the determination of what, if any, danger is present, as well as the formulation of a plan for removing the pollutant or preventing its further accumulation. Thus, the ability to quickly, easily, and accurately determine whether an environmental sample (soil, sediment, water, ashes, etc.) is contaminated with a specific toxicant can be of great importance to wastewater and water treatment plant operators, hazardous waste managers, health officials, and others who have an interest in protecting public health and the environment from toxic insult. Although sophisticated techniques for analyzing environmental samples are well known, these techniques are often costly, time consuming, and cannot be done in the field because instrumentation and extensive sample preparation are necessary. Moreover, these techniques do not indicate whether the sample is toxic to the biota.

As used herein, the term toxicants refers to compounds, elements, or other entities in an environmental sample which, alone or in combination, may be injurious to humans or other living things. As used herein, the term heavy metals refers to metals such as antimony (Sb), arsenic (As), beryllium (Be), cadmium (Cd), copper (Cu), chrominum (Cr), lead (Pb), mercury (Hg), nickel (Ni), selenium (Se), silver (Ag), tellurium (Te), and zinc (Zn). Existing methods for testing environmental samples for toxicants include both chemical and biological assays. Chemical assays whereby reagents are added to a test sample are well known. Chemical assays which are performed in the field often lack selectivity and provide ambiguous results. Of course, more sophisticated chemical assays can be performed in labroatories, but the sample preparation needed and expensive instrumentation limit the utility of these procedures. Recently, more attempts have also been made to develop biological toxicity assays. For example, several microbial assays have been developed for assessing chemical toxicity. These biological assays can be based on the effects of certain toxic chemicals on microorganisms. For example, toxic chemicals in a test sample may inhibit growth, respiration, motility, viability, enzyme activity or biosynthesis, bioluminescence, photosynthesis, heat production, and ATP. However, there are many obstacles which must be overcome in order to develop a biological assay that can accurately identify the presence of toxic agents. Specifically selected microbes must be found which have the desired sensitivity for toxicants. The toxicant must not only exert some type of biological effect on the microbe but, also, that effect must be easily detectable for the assay to have any utility. Finally, the effect of toxicants must be independent from any effect caused by non-toxicants. Before the current invention, no bioassay had been developed which could selectively detect the presence of specific toxicants in a sample.

BRIEF SUMMARY OF THE INVENTION

The subject invention is an assay and kit for the detection of toxicants in environmental samples such as water, wastewater, soil, sediment, and ashes. Specifically exemplified herein is an assay based on the specific inhibition of the enzyme beta-galactosidase by heavy metals. One of the primary advantages of this assay is that it is very selective for heavy metals. Organic and inorganic non-metal toxicants are not detected by this assay. Therefore, it is possible to rapidly differentiate between types of toxicants which may exist within a sample.

In one preferred embodiment of the invention, a specific beta-galactosidase-producing bacterium is used to supply the enzyme. The beta-galactosidase from this bacterium is highly and specifically sensitive to heavy metal toxicity. The bacterium is freeze-dried and then reconstituted before use, in this assay. A preferred embodiment further comprises the incorporation of a beta-galactosidase substrate onto an assay pad. Advantageously, a sample can be tested by simply mixing the reconstituted bacteria with a test sample and applying a small amount of the mixture to the test pad containing the enzyme substrate. Heavy metal toxicity is identified by observing color change or fluorescence intensity on the pad.

A further aspect of the invention is a kit which facilitates rapid, convenient detection of heavy metal toxicants. This kit comprises the bacterial reagent and assay pads. The kit may further comprise a diluent and buffer. The kit may further comprise confirmatory chemicals or supplies, data logger or encoder, and battery-operated incubator.

DETAILED DESCRIPTION OF THE INVENTION

The biological assay of the subject invention selectively detects the presence of heavy metals in an environmental sample. The sample can be, for example, water, soil, sediment, or ashes and does not have to go through extensive sample preparation. The presence of heavy metals is detected by observing the effect of the sample on beta-galactosidase activity. Beta-galactosidase is an enzyme which normally catalyzes the biochemical conversion of lactose to glucose and galactose. Beta-D-galactosidase (beta-D-galactoside galactohydrolase, lactase, E.C. 3.2.1.23) is extensively used in food and milk industries, agriculture, and medicine. Sweet syrup, prepared from whey, following lactose hydrolytic action, is used to sweeten ice cream, soft drinks, and bakery products. Bacteria, yeasts, fungi, plants, and some animal organs can serve as a source of beta-galactosidase. Another commercial source of beta-galactosidase is LACTAID TM, which is used for the degradation of lactose in milk for consumers suffering from beta-galactosidase deficiency. The properties (e.g., temperature and pH optima) of beta-galactosidase depend on the producing microorganism. For example, fungal lactases act at an acid range (pH=2.5-4.5) whereas the pH optima for yeast and bacterial lactases are 6-7 and 6.5-7.5, respectively. Optimal temperatures may also vary from 35°-40° C. for *E. coli* to 70° C. for the fungus *Alternaria alternaria*. The enzyme is often produced inside the cell, but some fungal species (e.g., *Fusarium moniliforme*) produce extracellular beta-galactosidase.

Beta-D-galactosidase catalyzes the hydrolysis of lactose and other galactosides. Lactose is hydrolyzed to glucose and galactose.

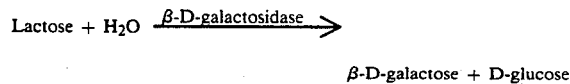

Glucose and galactose can be determined by conventional methods. Also, beta-galactosidase activity can be assayed utilizing special substrates which are converted into detectable (colored or fluorescent) compounds. For example, by using a substrate which fluoresces when it is hydrolyzed by beta-galactosidase, it is possible to assess the activity of the beta-galactosidase by measuring the release of fluorescence by the hydrolyzed substrate.

One such approach for the determination of beta-galactosidase consists of using methylumbelliferyl-beta-galactoside (MUGA) as a substrate and measuring the liberated methylumbelliferone via fluorescence. However, the most common assay for beta-galactosidase is based on the use of a synthetic chromogenic substrate, o-nitrophenyl-$\beta$-D-galactoside (ONPG). ONPG is hydrolyzed to o-nitrophenol, a yellow product which is measured spectrophotometrically at 420 nm. One enzyme unit is one micromole of nitrophenol liberated from ONPG/min.

It has been found that the presence of heavy metals inhibits beta-galactosidase activity. Therefore, in the example described above, fluorescence reduction resulting from exposure of beta-galactosidase to the test sample can be indicative of heavy metal pollution in the sample. Advantageously, it has been determined that beta-galactosidase activity is not inhibited by pollutants or toxicants other than heavy metals. Neither organic nor inorganic non-metal toxicants were found to inhibit beta-galactosidase activity. Although strong oxidants such as chlorine may slow beta-galactosidase activity, the effect of such compounds can be rapidly and conveniently eliminated by adding a reducing agent such as sodium thiosulfate. Therefore, the novel assay and kit described here provide very selective means for detecting the presence of heavy metals even when the metals are mixed with other toxicants.

The beta-galactosidase used in the assay of the subject invention can be supplied from a variety of sources. Specifically exemplified herein is beta-galactosidase which is produced by a microorganism. Certain strains of high-producers of beta-galactosidase are described.

In one preferred embodiment of the invention, the beta-galactosidase producing bacteria are freeze-dried so that they can be stored and later reconstituted for use in the assay. The freeze-drying process facilitates the shipping of the cells and also enhances the permeability of cells to toxicants, including heavy metals.

An important aspect of the subject invention is the provision of kits which facilitate the easy and accurate detection in the field of heavy metals in environmental samples. These kits comprise a source of beta-galactosidase and a substrate which is formulated and presented in such a fashion so as to enable the determination of beta-galactosidase activity. In one preferred embodiment of the novel kit, the kit comprises a pad into which an appropriate substrate has been incorporated. Such a substrate-containing pad is known as a TOXIPAD TM, and the assay is known as the TOXIPAD TM Assay. The assay is performed by simply mixing the analytical sample with a source of beta-galactosidase. As described above, the source of beta-galactosidase may be freeze dried (and reconstituted) beta-galactosidase-producing bacteria or other microorganism. If the sample is highly toxic, several dilutions of the sample may be tested using the TOXIPAD TM assay and a Minimum Inhibitory Concentration (MIC) may be determined. The diluent used can be deionized, activated-carbon treated, microfiltered water such as MilliQ TM. Following addition of the toxicant, a buffer may be added to ensure that the enzymatic assay is carried out under a constant pH.

A small amount of the solution with the beta-galactosidase and analytical sample is then applied to the TOXIPAD TM. Color change or fluorescence reduction can then be easily observed as the measure of beta-galactosidase activity. A lack or a reduction of such activity identifies the presence of heavy metals in the sample.

MATERIALS AND METHODS

Characteristic Enzyme Substrates Used in TOXIPAD TM. One substrate which can be used according to the subject invention is chlorophenol red-beta-D-galactopyranoside (CPRG), which can be purchased from Boehringer Mannheim Inc. The solubility of CPRG is more than 50 mmol/L. It is stable at $-20°$ C. and must be protected from light. CPRG was dissolved in 50 mM K-phosphate buffer containing 1 mM $MgCl_2$. The pH of the CPRG solution was 7.5 This solution is stable at 4° C. for one week. When the beta-galactosidase catalyzed hydrolysis of CPRG occurs, the resulting product on the TOXIPAD TM is purple and, thus, is easily detected visibly.

Another beta-galactosidase substrate which can be used is 4-methylumbelliferyl-beta-D-galactoside (MUGA), purchased from Sigma (Cat. #M-1633) and prepared at a concentration of 100 mg/L in 0.05M K-phosphate buffer, pH=7.5. This substrate release fluorescent umbelliferone when hydrolysed by beta-galactosidase.

Bacteria Used. As described above, one convenient source of beta-galactosidase is bacteria which produce this enzyme in useful amounts. Advantageously, the enzyme produced by the bacteria is readily accessible to the heavy metal and the substrate. Certain strains of *E. coli* have been found to function quite well in this regard. Among the bacteria investigated by the applicants are *E. coli* C3000, *E. coli* EW1b, and a mixed culture of beta-galactosidase producers isolated from wastewater. *E. coli* C3000 is available from the American Type Culture Collection (ATCC), 12301 Parklawn Drive, Rockville, Md. 20852 USA. The culture has been assigned the accession number ATCC 15597 by the repository. *E. coli* EW1b is available from the Coli Genetic Stock Culture, Yale University, New Haven, Conn. The mixed culture was obtained following inoculation of LB-lactose-SDS broth with activated sludge effluent. Although these bacteria would perform well in the assay of the subject invention, *E. coli* C3000 was not as sensitive to heavy metal toxicity as *E. coli* EW1b or the mixture of beta-galactosidase producing bacteria. Moreover, due to potential problems in maintaining a mixed culture of bacteria, *E. coli* EW1b is the preferred microbe. For optimal results, it was found that bacteria which produce high levels of enzyme are preferred. Advantageously, fewer bacteria cells need to be utilized when production of enzyme is high. It was found that use of fewer bacteria cells is not only economical, but also improves the performance of the assay. Production of the enzyme of interest can be enhanced by treating the bacteria with an appropriate inducer. It was discovered that beta-galactosidase production could be enhanced by treating *E. coli* EW1b cells with IPTG, for example.

The test bacteria were grown in Luria's Broth supplemented with 1% lactose and buffered with phosphate buffer. They were freeze-dried, using Flexy-Dry ® freeze-dryer purchased from FTS Systems, Stone Ridge, NY.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of Pads for Toxicity Testing

1. Optimum Enzyme Substrate Concentration Used for Soaking the Pads. As described above, the reaction of CPRG in the presence of beta-galactosidase results in the formation of purple coloring. In order to prepare the TOXIPAD ™ filter pads, or similar-type pads, they can be soaked in a solution comprising the substrate. With regard to optimum purple color development, we compared pads soaked in CPRG at concentrations of 100 or 200 ppm. Color development was superior in pads soaked in 200 ppm CPRG.

It was found that the optimum MUGA (fluorescence-producing substrate) concentration was 100 mg/L.

Filter pads from Gelman Sciences were soaked into a buffered solution of beta-galactosidase substrate (CPRG or MUGA). The pads were allowed to dry overnight at room temperature in the dark.

If so desired, the pads can also be soaked in a mixture of both substrates (CPRG+MUGA). Following reaction with the enzyme, these special pads can be observed under regular light (development of purple color) or under long-range UV light (development of fluorescent spots).

2. Stability of Filter Pads. Filter pads were soaked in buffered CPRG and incubated at room temperature, at 5° C. (refrigerator temperature), and at −15° C. A mixed culture of beta-galactosidase producing bacteria was used to test the stability of the pads (i.e., positive beta-galactosidase reaction indicated by the formation of a purple color). After various time periods, drops of bacterial cultures were spotted on the CPRG pads. The development of a purple color indicated a positive reaction.

The pads were tested after up to 4 weeks of storage. All the pads displayed a positive reaction (i.e., purple color) after storage at all temperatures investigated.

Recent testing has shown that the pads are stable for almost a year when stored in a refrigerator. Therefore, pads stored in the dark are stable and can be used after several months of storage at refrigerator temperature.

EXAMPLE 2

Bacteria Used in Toxipad

Freeze-Drying Conditions for Assay Bacteria. It is quite convenient to use freeze-dried bacteria in toxicity assay kits. The assay bacteria can be shipped conveniently and safely to any desired location.

It has been determined that assay bacteria freeze-dried in 12% sucrose are less sensitive to heavy metal toxicity than bacteria freeze-dried in trehalose medium (sucrose and trehalose media are cryoproptectants traditionally used for freeze-drying bacteria).

In subsequent experiments, we studied the effect of the freeze-drying medium (distilled water versus trehalose medium) on bacterial sensitivity to heavy metal toxicity. Table 1 shows that assay bacteria freeze-dried in trehalose (22.4% w/v) were more sensitive to heavy metals than bacteria freeze-dried in distilled water. However, it has also been determined that bacteria freeze-dried in 22.4% (w/v) trehalose medium cannot easily be resuspended. Therefore, the concentration of trehalose (22.4% w/v) was reduced to 11.2% (w/v).

Further modifications showed that bacteria can be freeze-dried in 2% trehalose and are easily resuspended in distilled water.

Thus, the preferred concentration of trehalose in the freeze-drying medium is 1% to 15%, and 2% is optimal.

EXAMPLE 3

Use of TOXIPAD ™ in the Specific Determination of Heavy Metal Toxicity

1. Heavy Metal Toxicity Using TOXIPAD ™. The toxicity of 7 heavy metals ($Cd^{2+}$, Cr (VI), $Cu^{2+}$, $Hg^{2+}$, $Pb^{2+}$, $Ni^{2+}$, and $Zn^{2+}$) commonly found in water and wastewater is displayed in Table 2. Metal toxicity is expressed as Minimum Inhibitory Concentration (MIC) or total inactivation. TOXIPAD ™ responds to all the heavy metals tested. Cadmium was the most toxic among the metals tested.

2. Heavy Metal Toxicity: Comparison Between Fluorescent and CPRG Pads. The sensitivity of detecting heavy metals using fluorescent pads as compared to CPRG pads was assessed. Table 3 shows that the fluorescent pads performed slightly better than CPRG pads.

3. Toxicity of Organic Toxicants Using TOXIPAD ™. The toxicity of nine organic compounds was tested using TOXIPAD ™. None of these chemicals exhibited any toxicity when assayed with TOXIPAD ™ (Table 4).

These results clearly demonstrate that the TOXIPAD ™ test is specific for heavy metal toxicity and does not respond to organic toxicity. This important feature allows distinction between heavy metal and organic toxicity when used in conjunction with a test for general toxicity such as MICROTOX ™.

TABLE 1

| Effect of suspending medium on sensitivity of *E. coli* EW1b to heavy metals. | | |
|---|---|---|
| HEAVY METAL | COLOR INTENSITY | |
| (ppm) | Distilled Water | Trehalose Medium |
| CONTROL | +++++* | ***** |
| Cadmium ($CdSO_4$) | | |
| 0.3 | ++++++ | ++ |
| 0.6 | ++++ | + |
| 1.0 | +++ | − |
| 1.5 | + | − |
| Copper ($CuSO_4.5H_2O$) | | |
| 0.5 | +++++ | ++ |
| 0.8 | +++++ | + |
| 1.0 | +++++ | − |
| 1.5 | +++++ | − |
| Lead ($Pb(NO_3)_2$) | | |
| 3.0 | | +++++ |
| 5.0 | | +++ |
| 7.0 | | ++ |

TABLE 1-continued

Effect of suspending medium on sensitivity of *E. coli* EW1b to heavy metals.

| HEAVY METAL (ppm) | COLOR INTENSITY | |
|---|---|---|
| | Distilled Water | Trehalose Medium |
| 10.0 | | + |
| 15.0 | | − |
| 20.0 | | − |
| Mercury (HgSO$_4$) | | |
| 0.5 | +++++ | ++++ |
| 1.0 | +++++ | − |
| 1.5 | +++++ | − |
| 2.0 | ++++ | − |
| Zinc (ZnSO$_4$) | | |
| 0.5 | +++++ | +++++ |
| 1.0 | +++++ | ++ |
| 3.0 | +++ | − |
| 5.0 | ++ | − |
| 7.5 | + | − |
| 10.0 | − | − |

*+++++ = maximum color intensity
− = complete enzyme inactivation

TABLE 2

Heavy metal toxicity using TOXIPAD.

| HEAVY METAL | MIC* | TOTAL INACTIVATION** |
|---|---|---|
| Cd (CdSO$_4$) | 0.2 | 1.0 |
| Cr (K$_2$Cr$_2$O$_7$) | 25.0 | 50.0 |
| Cu (CuSO$_4$.5H$_2$O) | 0.5 | 1.0 |
| Hg (HgSO$_4$) | 0.5 | 1.0 |
| Pb (Pb(NO$_3$)$_2$) | 5.0 | 15.0 |
| Ni (NiSO$_4$.6H$_2$O) | 8.0 | 20.0 |
| Zn (ZnSO$_4$) | 0.5–1 | 3.0 |

† All concentrations in mg/L.
*Minimum Inhibitory Concentration
**Toxicant concentration which causes 100% inhibition of enzyme activity

TABLE 3

Comparison between fluorescent and CPRG pads as regards the detection of heavy metal toxicity.

| Heavy Metal | MINIMUM INHIBITORY CONCENTRATION (MIC; mg/L) | |
|---|---|---|
| | Fluorescent Pads | CPRG Pads |
| Cadmium | 0.30 | 0.30 |
| Copper | 0.25 | 0.50 |
| Mercury | 0.25 | 0.25 |
| Nickel | 5.00 | 8.00 |
| Lead | 2.50 | 5.00 |
| Zinc | 0.50 | 0.5–1.00 |
| Chromium | 25.00 | 25.00 |

TABLE 4

Toxicity testing of organic compounds using TOXIPAD.

| TOXICANT | COLOR INTENSITY |
|---|---|
| CONTROL | +++++ |
| Pentachlorophenol (400 ppm)* | +++++ |
| Phenol (3000 ppm) | +++++ |
| Hydrothol (53 ppm) | +++++ |
| Formaldehyde** (925 ppm) | +++++ |
| Chloroform (3250 ppm) | +++++ |
| Lindane (500 ppm) | +++++ |
| p-nitrophenol (110 ppm) | +++++ |
| Sodium dodecyl sulfate (3000 ppm) | +++++ |
| Sonar (Fluoridone) (400 ppm) | +++++ |

*Maximum concentration tested at which no inhibition was observed
**Formaldehyde buffered to pH = 7.0 with K-phosphate buffer

EXAMPLE 4

Use of TOXIPAD ™ for the Determination of Heavy Metal Toxicity in Wastewater Samples Wastewater samples were taken from the collection system of the Buckman wastewater treatment plant in Jacksonville, Fla. Four out of five samples displayed toxicity when using TOXIPAD ™. Samples EX, MC, and CP, tested at 90% concentration level, caused 100% inhibition of bacterial beta-galactosidase. The SCM sample was also toxic (approximately 60% inhibition of the bacterial enzyme), using the CPRG pads. The GM sample was not toxic to the enzyme.

The fluorescent pads gave results similar to the CPRG pads.

Testing of industrial collection systems in Gainesville, Fla. showed that one sample out of four was toxic, using TOXIPAD ™.

EXAMPLE 5

The TOXIPAD ™ Kit

The TOXIPAD ™ kit comprises the following separately compartmentalized components:

(a) an assay pad comprising at least one enzyme substrate which is converted by the enzyme into a detectable compound; and (b) an enzyme which is selectively inhibited by the environmental toxicant which is to be detected.

The enzyme may be in a composition comprising freeze-dried bacteria which produce the enzyme. The kit may further comprise a diluent and buffer. The diluent may be MilliQ ™ or equivalent quality water. The buffer may be pH = 7.5 phosphate buffer. The kit may further comprise chemicals or resins for a confirmation step, and/or a portable incubator.

A. PREPARATION OF FREEZE-DRIED CELLS

1. Stock cultures of *E. coli* EW1b are stored in 40% glycerol solution at −14° C. to −20° C.

2. Fifty μL of the stock culture are inoculated into 5 ml of LB-lactose medium (Bacto-tryptone: 1%; yeast extract: 0.5%; NaCl: 1.0%; K$_2$HPO$_4$: 0.15%; Lactose: 1%).

3. Cells are grown overnight at 35° C. The bacterial suspension is then diluted with 20 ml of fresh medium, amended with 1 ml of 0.2% (w/v) solution of isopropyl-beta-thiogalactoside (IPTG) and then allowed to grow to absorbance $A_{550}$ = 0.4–0.5.

4. Cells are centrifuged at 8000 RPM for 10 minutes.

5. The pellet is resuspended in distilled water.

6. The suspension is centrifuged for 10 minutes at 8000 RPM.

7. The suspension is resuspended in 2% trehalose to obtain an absorbance of $A_{550}$ = 0.2–0.25 (if using the MUGA pads for enzyme assay, an absorbance of $A_{550}$ = 0.10 is sufficient).

8. This suspension is dispensed in 3 ml aliquots in serum bottles.

9. The cells are frozen overnight at −40° C.

10. The frozen cells are freeze-dried for 24 hours and stored at subzero or at refrigerator temperature until used. The beta-galactosidase activity of the freeze-dried cells is stable for several weeks at 4° C. Moreover, the enzyme was stable for at least 18 hours at 35° C.

11. For toxicity testing, the freeze-dried bacteria are rehydrated with 3 ml of MilliQ ™ or equivalent quality water. 0.1 ml of this bacterial suspension is added to 0.9 ml of toxic sample or dilution thereof.

B. PREPARATION OF FILTER PADS

1. CPRG Pads
   a. Prepare a 0.1% (w/v) CPRG stock solution in 50 mM K-phosphate buffer containing 1 mM Mg (pH=7.5).
   b. Filter-sterilize the CPRG solution via passage through a 0.2 μm filter. Store in the dark at 4° C. until used.
   c. CPRG pads are prepared by soaking filter pads into 200 ppm of CPRG solution (dilute stock solution into 50 mM K-phosphate buffer).
   d. Dry pads for 24 hours in the dark at room temperature.
   e. Store pads in sealed petri dishes in the refrigerator until used.
2. Fluorescent Pads
   a. Prepare a 0.1% (w/v) of methylumbelliferyl beta-D-galactoside (MUGA) stock solution 0.05M K-phosphate buffer (pH=7.5).
   b. Filter-sterilize the MUGA solution via passage through a 0.2 μm filter. Store in the dark at 4° C. until used.
   c. Fluorescent pads are prepared by soaking filter pads into 100 ppm of MUGA solution.
   d. Dry pads for 24 hours in the dark at room temperature.
   e. Store pads in sealed petri dishes in the refrigerator until used.

EXAMPLE 6

TOXIPAD TM Methodology

1. Freeze-dried *E. coli* EW1b (bacterial reagent) cells are rehydrated in 3.0 ml MilliQ TM or equivalent quality water (diluent). The absorbance ($A_{550}$) of the bacterial suspension is 0.20–0.25.
2. Mix suspension for 1 minute, incubate for 10 minutes at room temperature, and mix again.
3. Add 0.1 ml of the cell suspension to 0.9 ml of sample. Add 0.9 ml of MilliQ TM or equivalent quality water or other appropriate control medium to the control tube.
4. Shake the mixture and incubate at 35° C. for 90 minutes.
5. Add 0.1 ml of 0.3M K-phosphate buffer, pH=7.5 (buffer) and mix.
6. Dispense one drop of mixture on CPRG pad or MUGA pad (assay pad). Incubate for 30 minutes at 35° C. for color or fluorescence development.
7. Observe the intensity of the purple color (if CPRG pad is used) or fluorescence intensity (if MUGA pad is used).

The fluorescence of the spots on the pads is observed using a Black-Ray Lamp, model UVL-21 (UVP, Inc., San Gabriel, CA), which emits long range UV at 366 nm.

The intensity of purple spots on a CPRG-impregnated pad indicates the activity of beta-galactosidase and, thus, the heavy metal toxicity in a given sample.

TOXIPAD assay is performed in 9 steps as follows:
1. Add 1.0 ml of diluent to serum bottle containing the bacterial reagent.
2. Mix thoroughly for 1 minute, let stand for 10 minutes, and mix again.
3. Add 0.1 ml of bacterial suspension to 0.9 ml of sample in assay tubes.
4. Shake assay tubes for one minute.
5. Incubate for 90 minutes at 35° C.
6. Add 0.1 ml buffer and shake.
7. Dispense drops of mixtures onto assay pads.
8. Incubate for 30 minutes at 35° C.
9. Observe purple color or fluorescence intensity and compare to control.

EXAMPLE 7

The assay of the subject invention may further comprise a confirmation step whereby the presence of the toxicant of interest can be verified. For example, in the case of heavy metals, the confirmation step may comprise the addition of a chelating or precipitating agent in the environmental sample. One such reagent which could be added is TMT. Other reagents which would perform this function are well known to those skilled in the art.

An additional confirmation step could comprise passing the environmental sample or extract through a chelating or a cation exchange resin followed by testing with the TOXIPAD TM assay. The resin would remove any heavy metals in the sample, and the subsequent TOXIPAD TM assay would then be expected to give a negative result.

The TOXIPAD TM kit could include chemicals or resins needed for the confirmation step.

EXAMPLE 8

A further aspect of the subject invention pertains to the preservation of the assay pad via lamination between a translucent material such as plastic. This process can be combined with procedures for encoding certain relevant data onto the pad or the laminated pad. For example, a bar encoder can be used to encode data relating to the date and location of a sample and any other identifying characteristics. The information can subsequently be retrieved with a bar decoder and transmitted to a computer for entry in a program for recording results. The bar encoder may be included in a TOXIPAD TM kit.

We claim:

1. An assay pad useful for detecting the presence of heavy metal toxicants in an environmental sample, said pad comprising one or more enzyme substrates selected from the group consisting of MUGA and CPRG which, when acted upon by an enzyme, are converted to compounds which can be detected on said pad.

2. The assay pad, according to claim 1, wherein said substrates are converted either to fluorescent or colored compounds when acted upon by said enzyme.

3. The assay pad, according to claim 1, wherein said pad is prepared by soaking a filter-type pad in a solution of CPRG or MUGA wherein the concentration of CPRG or MUGA is between about 50 and about 250 ppm.

4. The pad, according to claim 3, wherein the concentration of said solution of CPRG is about 200 ppm.

5. The pad, according to claim 3, wherein the concentration of said solution of MUGA is about 100 ppm.

6. A kit for the detection of toxicants in an environmental sample, said kit comprising the following separately compartmentalized components:
   (a) an assay pad comprising at least one enzyme substrate which is converted by the enzyme into a detectable compound; and (b) an enzyme which is selectively inhibited by the environmental toxicant which is to be detected.

7. The kit, according to claim 6, wherein said enzyme is present in a solution which comprises bacteria which produce said enzyme.

8. The kit, according to claim 7, wherein said bacteria have been freeze-dried and reconstituted.

9. The kit, according to claim 6, wherein said enzyme is selected from the group consisting of beta-galactosidase, α-galactosidase, phosphatase, and urease.

10. The kit, according to claim 9, wherein said enzyme is beta-galactosidase.

11. The kit, according to claim 7, wherein said enzyme is beta-galactosidase and said bacteria are selected from the group consisting of *E. coli* EW1b and *E. coli* C3000.

12. The kit, according to claim 6, wherein said substrate is converted to a colored or fluorescent product.

13. The kit, according to claim 12, wherein said substrate is selected from the group consisting of CPRG and MUGA.

* * * * *

UNITED STATES PATENT AND TRADEMARK OFFICE
CERTIFICATE OF CORRECTION

PATENT NO.   :   5,149,656

DATED        :   September 22, 1992

INVENTOR(S)  :   Gabriel Bitton, Ben Koopman

It is certified that error appears in the above-identified patent and that said Letters Patent is hereby corrected as shown below:

Column 1, line 4, insert, --This invention was made with government support under NSF Grant No. CES-8619073. The government has certain rights in this invention.--
Column 4: line 39: "release" should read --releases--.
Column 7: line 25 (Table 2): "TOXIPAD" should read --TOXIPAD†--.

Signed and Sealed this

Fourteenth Day of September, 1993

Attest:

BRUCE LEHMAN

*Attesting Officer*              *Commissioner of Patents and Trademarks*